(12) United States Patent
Chen et al.

(10) Patent No.: US 10,390,763 B2
(45) Date of Patent: Aug. 27, 2019

(54) METHOD, SYSTEM, NON-TRANSITORY COMPUTER-READABLE MEDIUM AND COMPUTER PROGRAM PRODUCT FOR CALIBRATING TIME OF PHYSIOLOGICAL DATA

(71) Applicant: TAIDOC TECHNOLOGY CORPORATION, New Taipei (TW)

(72) Inventors: Chao-Wang Chen, New Taipei (TW); How-Ray Sung, New Taipei (TW)

(73) Assignee: TAIDOC TECHNOLOGY CORPORATION, New Taipei (TW)

( * ) Notice: Subject to any disclaimer, the term of this patent is extended or adjusted under 35 U.S.C. 154(b) by 208 days.

(21) Appl. No.: 15/593,321

(22) Filed: May 12, 2017

(65) Prior Publication Data

US 2018/0271451 A1    Sep. 27, 2018

(30) Foreign Application Priority Data

Mar. 21, 2017  (TW) .............................. 106109232 A

(51) Int. Cl.
*A61B 5/00* (2006.01)
*G01D 18/00* (2006.01)
(Continued)

(52) U.S. Cl.
CPC .......... *A61B 5/7235* (2013.01); *A61B 5/0017* (2013.01); *A61B 5/0022* (2013.01); *A61B 5/01* (2013.01); *A61B 5/021* (2013.01); *A61B 5/0402* (2013.01); *A61B 5/14532* (2013.01); *A61B 5/14542* (2013.01); *G16H 50/20* (2018.01); *G16H 50/30* (2018.01);
(Continued)

(58) Field of Classification Search
CPC ... A61B 5/7235; A61B 5/14532; A61B 5/021; A61B 5/14542; A61B 5/0022; A61B 5/0017; A61B 5/01; A61B 5/0402; A61B 2560/0228; A61B 2560/023; G16H 10/00; H04W 76/10
See application file for complete search history.

(56) References Cited

U.S. PATENT DOCUMENTS 9,578,903 B2 *  2/2017  Cobbett ............... A61B 5/0205
10,004,413 B2 *  6/2018  Bokan .................. A61B 5/0422
(Continued)

*Primary Examiner* — Mohammad K Islam
(74) *Attorney, Agent, or Firm* — Chun-Ming Shih

(57) ABSTRACT

The present disclosure is related to a method, a system, a non-transitory computer-readable medium and a computer program product for calibrating time of a physiological data. The method includes providing a physiological monitoring device for storing a physiological data with a first measurement time, and the physiological monitoring device has a first counting time. A wireless communication channel is established between the physiological monitoring device and a time calibration device having a second counting time. The first counting time and the second counting time are compared to obtain a counting time deviation value, and the counting time deviation value is compared with a predetermined time deviation value. If the counting time deviation value exceeds the predetermined time deviation value, the first measurement time and the counting time deviation value are computed to obtain a calibrated measurement time of the physiological data.

26 Claims, 3 Drawing Sheets

(51) Int. Cl.
*A61B 5/01* (2006.01)
*A61B 5/0402* (2006.01)
*A61B 5/145* (2006.01)
*A61B 5/021* (2006.01)
*G16H 50/30* (2018.01)
*G16H 50/20* (2018.01)
*H04W 76/10* (2018.01)
*G16H 20/30* (2018.01)

(52) U.S. Cl.
CPC ............. *A61B 2560/0228* (2013.01); *A61B 2560/0238* (2013.01); *G16H 20/30* (2018.01); *H04W 76/10* (2018.02)

(56) References Cited

U.S. PATENT DOCUMENTS

| | | | |
|---|---|---|---|
| 10,314,547 B2 * | 6/2019 | Miller | A61B 5/7221 |
| 2005/0103351 A1 * | 5/2005 | Stomberg | A61N 1/025 |
| | | | 128/898 |
| 2011/0152769 A1 * | 6/2011 | Ramey | A61M 5/14244 |
| | | | 604/151 |
| 2014/0266785 A1 * | 9/2014 | Miller | H04B 5/0043 |
| | | | 340/870.04 |
| 2015/0073241 A1 * | 3/2015 | Lamego | A61B 5/0002 |
| | | | 600/327 |
| 2015/0087936 A1 * | 3/2015 | Al-Ali | A61B 5/0205 |
| | | | 600/309 |
| 2016/0058328 A1 * | 3/2016 | Hotta | A61B 5/7264 |
| | | | 600/508 |
| 2016/0170710 A1 * | 6/2016 | Kim | G06F 3/167 |
| | | | 704/275 |
| 2016/0345874 A1 * | 12/2016 | Raisoni | A61B 5/002 |
| 2017/0222961 A1 * | 8/2017 | Beach | H04L 51/16 |

* cited by examiner

METHOD, SYSTEM, NON-TRANSITORY COMPUTER-READABLE MEDIUM AND COMPUTER PROGRAM PRODUCT FOR CALIBRATING TIME OF PHYSIOLOGICAL DATA

BACKGROUND OF THE INVENTION

Field of the Invention

The present invention generally relates to a method, a system, a non-transitory computer-readable medium and a computer program product for calibrating time of a physiological data, and especially relates to a method, a system, a non-transitory computer-readable medium and a computer program product for calibrating time of a physiological data, through which a connection with a time calibration device can be established for comparing the counting time between the time calibration device and a physiological monitoring device to obtain a counting time deviation value, and the deviation value is further compared with a predetermined time deviation value to determine if calibration is required.

Description of Related Art

With the development of medical technology and raising awareness of personal health, application of electronic physiological monitoring devices become more prevalent at home, care centres, clinics or hospitals. Nowadays, changes in lifestyles have contributed to an increased number of chronic disease patients, such as patients with diabetes or high blood pressure. An electronic physiological monitoring device is required for regularly monitoring a specific physiological parameter, such that a medication can be administered based on the physiological data. Therefore, in addition to the accuracy of a physiological data, it is also important to obtain a correct measurement time of the physiological data.

Nowadays many electronic devices have a timer function. Take a smart phone for example, its microprocessor may have a timer function or an independent timer module may be incorporated therein. When being connected with a server, time of the server can be obtained for calibration. However, while smart phones usually have multiple functions, frequent connections for time calibration may consume lots of electricity and selling price can be high.

On the other hand, selling price of a general physiological monitoring device is usually less than a smart phone, especially for a home-use physiological monitoring device. For introducing more products to the market, the price cannot be high. Therefore, cost of the product itself should be lower. For example, although the microprocessor used in a physiological monitoring device is similar to that used in a smart phone, it may not have such high standards as used in the smart phone.

Besides, different from the multifunctional smart phones, the main function of a physiological monitoring device is to measure a physiological parameter accurately, and to obtain an accurate measurement time for the physiological parameter. Take an ear thermometer or a blood glucose meter for example, usually the meter is much more often in shutdown mode or standby/sleep mode than in performing measurements. Thus, it does not have many chances to connect and perform time calibration as compared with a smart phone.

Furthermore, different from the completed interfaces of smart phones for touch operations, a physiological monitoring device requires only a simple operation interface. Users of home-use physiological monitoring devices are often older people. Take a blood glucose meter as an example, the whole device may only have a single button. It's quite difficult for an elder user to set four-digit years, two-digit month(s), date, hour(s) and minute(s) just by a single button.

Based on above, a physiological monitoring device may not have a high standard microprocessor as used in a smart phone and may be limited by infrequent and short connections. However, in order to record the measuring time of the physiological data accurately, it requires higher accuracy in recording time than a mobile phone.

When turning on a physiological monitoring device for the first time, a user needs to set time on his/her own, or to correct the time of the device itself, such that future measurements for obtaining physiological data will have correct time records. Such data recording can be used as a basis for evaluating the medication. For example, a diabetic patient may need to inject insulin or oral medications, and the recorded data may help the physician who prescribes medications to observe long-term developments and to timely modify the treatments in view of physiological conditions. Besides, manually setting the local time is not convenient and may increase the risk of errors. However, to make sure each one of the physiological monitoring devices having an accurate time is difficult. It is because of the ability of the inner working elements in the physiological monitoring device may deplete due to time elapse after starting to use the physiological monitoring device, especially the most important functions as time counting, and therefore do not sure the efficiency of time counting unit in the physiological monitoring device whether deteriorate, or the microprocessor which executes multiple functions at the same time, including time counting, may induce time delay. Furthermore, the mild time inaccuracy is hard to observe, but the time will still be delayed after accumulating a long period. Accordingly, the counting time of the physiological monitoring device usually has time error problems based on the reasons described above.

In addition, under the situation that the physiological monitoring device runs out of power and change of battery is required, or the user removes the battery for saving energy in the long run, time counting function in the physiological monitoring device stops, and continues to count time or restarts time counting only when the power recovers. This will lead to counting time delay or even serious errors, and the measured physiological data recorded thereafter will also have incorrect time. When reviewing the history measurement records, the physician may be unable to interpret the data because of chaotic records of the measurement time, such that diagnosis may be delayed and the condition may be worsened. In some serious cases, the prime treatment time may be missed, and the patient's life may be threatened. Therefore, in addition to calibrate the counting time of a physiological monitoring device itself to avoid generating physiological data with wrong time records in the future, it's also important to retrospectively calibrate the time records of existing physiological data.

In the past, accept the physiological data and time thereof recording from the physiological monitoring device instead of having intent to calibrate the time of the existing records is due to ignore the possibility that the physiological monitoring device may have time error issue. However, if the connection and calibration are conducted through wired connections, it will increase the cost of additional transmission lines from the aspect of manufacture. From the aspect of design, take a blood glucose meter for example, if the strip insertion slot is used as a transmission port, it will be unable to use the detection function of the meter when the transmission line is connected. On the other hand, if the strip insertion slot is not used as a transmission port, it will need to open another hole on the housing of the meter. This will increase the production cost of the mold. From the aspect of usage, damage on the transmission line may result in failure of time calibration or transmission. Also, the portable range of the physiological monitoring device during transmission will be limited.

Therefore, for related manufacturers, how to establish a system and a method for calibrating the time of a physiological monitoring device conveniently and to provide a standard range for the calibration of the physiological monitoring device have become issues waiting to be further improved, so as to prevent the user from troublesome time-setting operations such as repeatedly updating the time or errors caused by manual entry, and to provide complete and correct physiological data records.

SUMMARY OF THE INVENTION

For improving deficiencies described above, a system for calibrating time of a physiological data is provided. Based on a rule of comparing counting time of a time calibration device and a predetermined time deviation value, wrong information of time of a physiological data and the physiological monitoring device can be corrected, such that accuracy of the data records can be increases and long-term reliability of data analysis can be elevated.

A method for calibrating time of a physiological data is provided. By comparing counting time of a physiological monitoring device and a time calibration device to obtain a deviation value, and then comparing the predetermined time deviation value, a rule for time calibration is established. Particularly, through a wireless communication channel, situations that a user forgets to update the correct time or needs to update time over and over again after the power of the physiological monitoring device recovers can be avoided. By providing healthcare professionals with physiological data having correct time records, the treatment plan can be modified in time.

A system for calibrating time of a physiological data is provided. While the design of physiological monitoring device is innately limited in view of manufacture, cost and usage, a wireless communication channel is provided as a route for time calibration. By automatically importing the calibrated time, the portable range of the physiological monitoring device during transmission and import can be wider, and the inconvenience for an elder user to set time by a single button can be eliminated.

A non-transitory computer-readable medium having an internally-stored program and a computer program product are provided. A time zone range can be obtained by identifying a production number of the physiological monitoring device, and loaded into the physiological monitoring device, so as to establish a counting time for the first time. Troublesome procedures for manual setting or possibility of errors can be eliminated.

For achieving above purposes, a method for calibrating time of a physiological data is provided, which is adapted to a physiological monitoring device for measuring at least one physiological parameter. The method comprises may comprise: providing the physiological monitoring device comprising a memory for storing a physiological data with a first measurement time, and the physiological monitoring device having a first counting time; establishing a wireless communication channel between the physiological monitoring device and a time calibration device having a second counting time; comparing the first counting time and the second counting time to obtain a counting time deviation value; comparing the counting time deviation value with a predetermined time deviation value; and calibrating the first measurement time of the physiological data, wherein when the counting time deviation value exceeds the predetermined time deviation value, the first measurement time and the counting time deviation value are computed to obtain a calibrated measurement time of the physiological data.

According to an embodiment of the present invention, calibrating the first measurement time of the physiological data further comprises when the counting time deviation value does not exceed the predetermined time deviation value, there is no need to calibrate the first measurement time and the first counting time.

According to an embodiment of the present invention, unit of the predetermined time deviation value is year(s), month(s), day(s), hour(s), minute(s), second(s), any combination thereof or any time unit which the time calibration device or the physiological monitoring device can recognize.

According to an embodiment of the present invention, the calibrated measurement time obtained from computing the first measurement time and the counting time deviation value is obtained from addition or subtraction of the first measurement time and the counting time deviation value.

According to an embodiment of the present invention, the wireless communication channel may be an infrared, Wi-Fi, Bluetooth, ANT, Zigbee, RFID, NFC, GSM, GPRS, UMTS, LTE, CDMA, any combination thereof or any wireless communication technology based on the optics, the magnetics or the electromagnetism and the wireless communication channel may be simplex communication, half-duplex communication or duplex communication.

According to an embodiment of the present invention, before or after the step of establishing the wireless communication channel between the physiological monitoring device and the time calibration device may further comprise calibrating the second counting time of the time calibration device to a standard time, and the standard time comes from a network server.

According to an embodiment of the present invention, after the step of establishing the wireless communication channel between the physiological monitoring device and the time calibration device may further comprise transmitting the physiological data to the time calibration device.

According to an embodiment of the present invention, the physiological parameter may be obtained by performing a measurement directly on a living body or on an in vitro sample obtained from a living body. According to an embodiment of the present invention, the physiological parameter is glucose, ketone, blood cell, blood pressure, haemoglobin, glycated haemoglobin (HbA1c), cholesterol, uric acid, urinary protein, lactate, temperature, body weight, blood oxygen level, hormone, electrocardiogram or any combination thereof.

According to an embodiment of the present invention, when the counting time deviation value exceeds the predetermined time deviation value, the first counting time is calibrated to the second counting time.

According to an embodiment of the present invention, further comprising comparing the counting time deviation value and a second predetermined time deviation value, wherein the first counting time is calibrated to the second counting time when the counting time deviation value exceeds the second predetermined time deviation value.

According to an embodiment of the present invention, the physiological monitoring device further comprises a production number, and after establishing the wireless communication channel, a time zone is obtained by the time calibration device based on the production number; and the first counting time of the physiological monitoring device is established based on the time zone.

Viewed from another aspect, a system for calibrating time of a physiological data is provided, which may comprise a physiological monitoring device comprising a measurement module for measuring at least one physiological parameter, a first timer module with a first counting time, and a memory for storing a physiological data with a first measurement time; a time calibration device comprising a second timer module with a second counting time and a microprocessor coupled to the second timer module; and a communication module for establishing a wireless communication channel between the physiological monitoring device and the time calibration device; wherein when the wireless communication channel is established, the microprocessor is used for comparing the first counting time and the second counting time to obtain a counting time deviation value, and comparing the counting time deviation value with a predetermined time deviation value, and when the counting time deviation value exceeds the predetermined time deviation value, the first measurement time and the counting time deviation value are computed to obtain a calibrated measurement time of the physiological data.

According to an embodiment of the present invention, unit of the predetermined time deviation value is year(s), month(s), day(s), hour(s), minute(s), second(s), any combination thereof or any time unit which the time calibration device or the physiological monitoring device can recognize.

According to an embodiment of the present invention, the calibrated measurement time obtained from computing the first measurement time and the counting time deviation value by the microprocessor is obtained from addition or subtraction of the first measurement time and the counting time deviation value.

According to an embodiment of the present invention, the wireless communication channel is an infrared, Wi-Fi, Bluetooth, ANT, Zigbee, RFID, NFC, GSM, GPRS, UMTS, LTE CDMA, any combination thereof or any wireless communication technology based on the optics, the magnetics or the electromagnetism and the wireless communication channel is simplex communication, half-duplex communication or duplex communication.

According to an embodiment of the present invention, the time calibration device is an electronic device which can obtain a standard time coming from a network server.

According to an embodiment of the present invention, the wireless communication channel is used for transmitting the physiological data from the physiological monitoring device to the time calibration device.

According to an embodiment of the present invention, the physiological parameter is obtained by performing a measurement directly on a living body or on an in vitro sample obtained from a living body.

According to an embodiment of the present invention, the microprocessor compares the counting time deviation value with the predetermined time deviation value, and when the counting time deviation value does not exceed the predetermined time deviation value, the microprocessor determines not to calibrate the first measurement time and the first counting time.

According to an embodiment of the present invention, the microprocessor compares the counting time deviation value and the predetermined time deviation value, and when the counting time deviation value exceeds the predetermined time deviation value, the microprocessor calibrates the first counting time to the second counting time.

According to an embodiment of the present invention, the microprocessor further compares the counting time deviation value and a second predetermined time deviation value, and when the counting time deviation value exceeds the second predetermined time deviation value, the microprocessor calibrates the first counting time to the second counting time.

According to an embodiment of the present invention, the physiological monitoring device may have a production number, and the time calibration device is used for obtaining a time zone based on the production number, and the first timer module is used for establishing the first counting time based on the time zone.

Viewed from another aspect, a non-transitory computer-readable medium having an internally-stored program is provided, which performs a method for calibrating time of a physiological data when being executed in a microprocessor. The method may include the following steps: establishing a wireless communication channel between a physiological monitoring device and a time calibration device, wherein the physiological monitoring device has a first counting time, the time calibration device has a second counting time, and the physiological monitoring device is used for storing a physiological data with a first measurement time; comparing the first counting time and the second counting time to obtain a counting time deviation value; comparing the counting time deviation value with a predetermined time deviation value; and calibrating the first measurement time of the physiological data, wherein when the counting time deviation value exceeds the predetermined time deviation value, the first measurement time and the counting time deviation value are computed to obtain a calibrated measurement time of the physiological data.

According to an embodiment of the present invention, unit of the predetermined time deviation value is year(s), month(s), day(s), hour(s), minute(s), second(s), any combination thereof or any time unit which the time calibration device or the physiological monitoring device can recognize.

According to an embodiment of the present invention, the calibrated measurement time obtained from computing the first measurement time and the counting time deviation value is obtained from addition or subtraction of the first measurement time and the counting time deviation value.

According to an embodiment of the present invention, after comparing the counting time deviation value with the predetermined time deviation value, when the counting time deviation value does not exceed the predetermined time deviation value, there is no need to calibrate the first measurement time and the first counting time.

According to an embodiment of the present invention, when the counting time deviation value exceeds the predetermined time deviation value, the first counting time is calibrated to the second counting time. According to an embodiment of the present invention, comparing the first counting time and the second counting time to obtain a counting time deviation value may further comprise comparing the counting time deviation value and a second predetermined time deviation value, and when the counting time deviation value exceeds the second predetermined time deviation value, the first counting time is calibrated to the second counting time.

According to an embodiment of the present invention, after establishing the wireless communication channel, a time zone is obtained based on a production number of the physiological monitoring device; and the first counting time of the physiological monitoring device is established based on the time zone.

Viewed from another aspect, a computer program product for calibrating time of a physiological data is provided, which completes the above methods after being loaded and executed by a computer.

Based on above, a method, a system, a non-transitory computer-readable medium and a computer program product for calibrating time of a physiological data provided in the present disclosure use a wireless communication channel as a route for comparing counting time of a time calibration device and a physiological monitoring device, such that inconvenience of setting multi-digits date or time by few buttons or a single button is eliminated. Additional cost of transmission lines is avoided, and the risk of damage on the transmission lines which results in functional failure is also eliminated. In addition, the applicable range and the portable range of the physiological monitoring device when performing time calibration can be wider. At the meantime, reliability of history physiological data is increased through transmission and calibration of time records of the physiological data. Furthermore, the counting time of the physiological monitoring device can also be calibrated, such that additional steps for calibrating time of the device can be omitted and convenience of usage can be improved. Also, the initial time settings of the physiological monitoring device can be completed by obtaining a time zone based on a production number, so as to decrease the steps for initial settings and increase the accuracy of time.

In order to make the aforementioned features and advantages of the present invention more comprehensible, the following embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

As described above, when using a conventional physiological monitoring device at first time, a user needs to set time. However, the entering steps for a user are very complex and there may be risk of errors when entering time manually. In addition, under the situation that the physiological monitoring device runs out of power or the user removes the battery, the device will restart time counting or there will be a counting time delay. This may result in incorrect time records for physiological data measured thereafter, and the user needs to reset time of the device over and over again. For a patient who needs to record medication or for a physician who needs to diagnoses based on the records, the best timing for medication may be missed, or the patient's condition may be misdiagnosed.

In contrast, in some embodiments of the present disclosure, counting time of a time calibration device and that of a physiological monitoring device is compared through a wireless communication channel. When the counting time of both the time calibration device and the physiological monitoring device exceeds a predetermined time deviation value, a physiological data with a calibrated time is obtained. Furthermore, the counting time of the physiological monitoring device can be further calibrated. In particular, in initial time setting of the physiological monitoring device, a corresponding time zone can be obtained by a production number through the wireless communication channel, such that complex steps for manual entering can be omitted and possibilities of entering incorrect time can be eliminated. Embodiments of the present invention will be described in further details below in reference to the accompanying figures. The accompanying figures illustrate exemplary embodiments of the present invention, in which the same reference sign indicates the same or a similar element.

Figure 1:
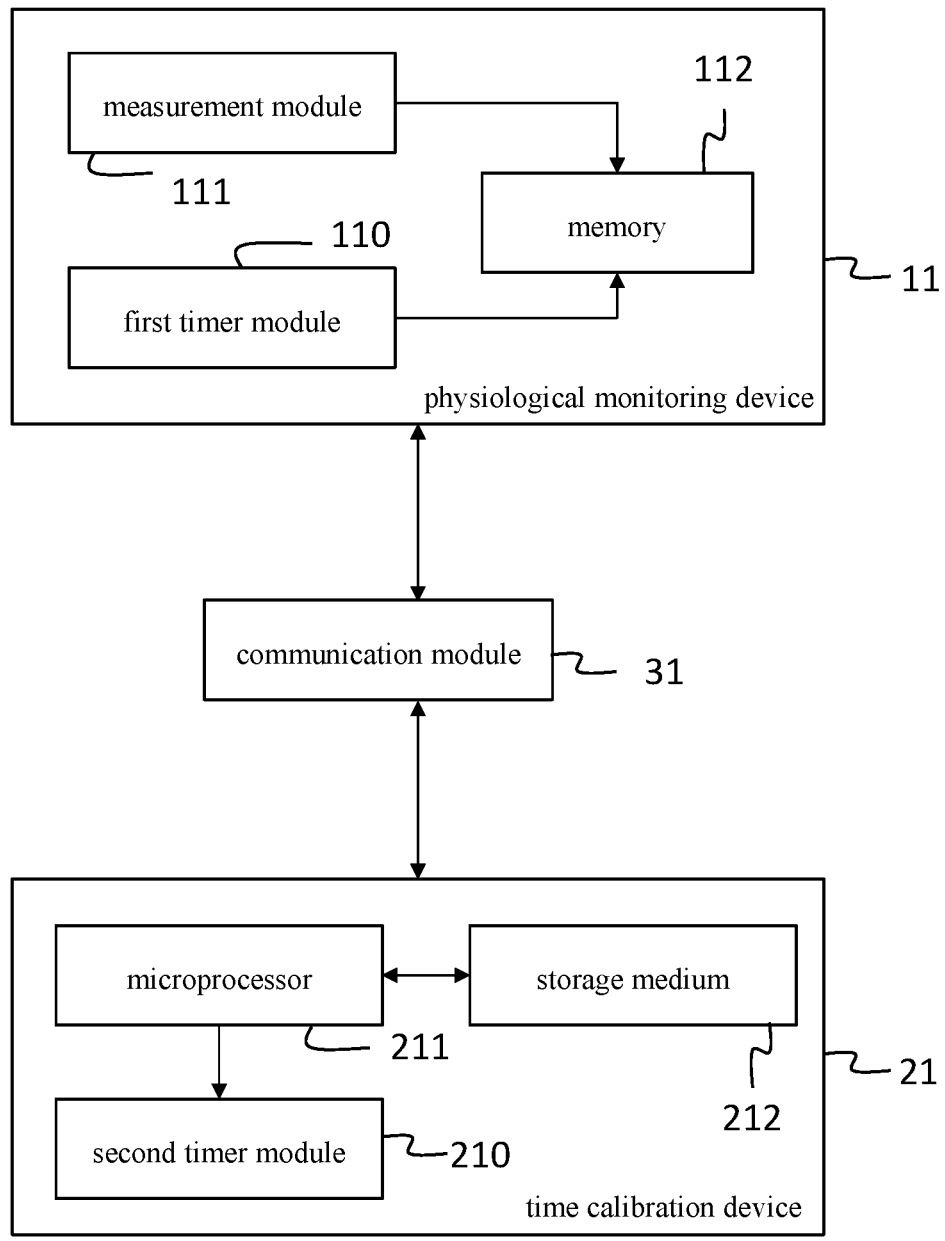
FIG. 1 is a functional block diagram of a preferred embodiment of a system for calibrating time of a physiological data according to the present invention.

FIG. 1 is a functional block diagram of a preferred embodiment of a system for calibrating time of a physiological data according to the present invention. Please refer to FIG. 1, in the embodiment, the invention provides a system (10) for calibrating time of a physiological data. The system comprises a physiological monitoring device (11), a time calibration device (21), and a communication module (31). Preferably, the physiological monitoring device (11), the time calibration device (21) and the communication module (31) can be separate devices. Specifically, the physiological monitoring device (11), the time calibration device (21), and the communication module (31) are three independent devices; however, the invention is not limited thereto. The system (10) for calibrating time of a physiological data can also be an integrated one-piece device. For example, the communication module (31) and the physiological monitoring device (11) may be integrally formed as one device, or the communication module (31) and the time calibration device (21) may be integrally formed as one device.

The physiological monitoring device (11) comprises a measurement module (111), a first timer module (110) and a memory (112). The measurement module (111) is used for measuring at least one physiological parameter. Preferably, the physiological parameter may be obtained by performing a measurement directly on a living body, and the living body may include but not limited to human, animal, plant and so on; for example, a measurement of heart rates, pulses, blood pressure, blood oxygen ($SpO_2$), electrocardiography (ECG), temperature, body weight, body fat, number of steps, respiratory flow, or a record of parameters related to a growth curve of the living body. Or, the physiological parameter may be obtained by performing a measurement on an in vitro sample obtained from a living body. The in vitro sample comprises but not limited to blood, urine, blood plasma, blood serum, cerebro-spinal fluid, spinal fluid or other body fluid. More preferably, the physiological parameter may be blood glucose, ketone, blood cell, haemoglobin, glycated haemoglobin (HbA1c), cholesterol, uric acid, urinary protein, lactate, hormone or other targets for detecting liver function. However, the present invention is not limited thereto. More specifically, after conducting a measurement by the physiological monitoring device (11), one or more physiological data record may be obtained.

The first timer module (110) has a first counting time. More specifically, the first timer module (110) is a clock of the physiological monitoring device (11), and the first counting time is used for indicating time of the physiological monitoring device (11). Preferably, the first counting time can be reset. In other words, the physiological data obtained by performing a measurement through the physiological monitoring device (11) has a corresponding measurement time and/or duration. The occurrence time, interval time or duration regarding every physiological data can be inquired through history records and can be used for tracking health condition of a user and for assisting the physician to observe the trends in a patient's condition.

The memory (112) is used for storing the physiological data. More specifically, the memory (112) is used for storing the value of the physiological data and its corresponding measurement time, or the duration of measurement. Preferably, the memory (112) may be any carrier capable of storing information. More preferably, the memory (112) may be a non-volatile memory. For example, the memory (112) can be a flash memory, disk, removable SD card, or Electrically-Erasable Programmable Read-Only Memory (EEPROM) which directly embedded in a circuit board. However, the invention is not limited thereto.

The time calibration device (21) is an electronic device which performs data processing based on an instruction. Preferably, the time calibration device (21) is an electronic device which can obtain a standard time. For example, the time calibration device (21) obtains the standard time from a network server by internet, but the way of the time calibration device (21) obtaining the standard time shall not be limited thereto; a person skilled in the art can change the way as needed. More preferably, the time calibration device (21) is a personal computer, a notebook computer, a pad computer, a mobile phone, a personal digital assistant (PDA), a smart appliance, a home video game console, a digital camera, or a network server; however, the invention is not limited thereto. The time calibration device (21) comprises a second timer module (210), a microprocessor (211), and a storage medium (212). The second timer module (210) has a second counting time. More specifically, the second timer module (210) is a clock of the time calibration device (21) and the second counting time is used for indicating the time of the time calibration device (21).

The microprocessor (211) is disposed in the time calibration device (21) for comparing the first counting time and the second counting time to obtain a counting time deviation value, and for further comparing the counting time deviation value and a predetermined time deviation value, so as to determine whether to calibrate the time of the physiological data and/or the time of the physiological monitoring device (11). The determining method will be described in detail below. Preferably, the microprocessor may be a central processing unit (CPU), a multi-processor, distributed data processing system and/or any suitable microprocessor.

The storage medium (212) is coupled to the microprocessor (211). The storage medium contains a computer program for performing a method for calibrating time of a physiological data in the microprocessor (211). However, the invention is not limited thereto, and the method for calibrating time of a physiological data will be described in detail below. Preferably, the storage medium (212) is an electromagnetic, optical, electronical, a magnetic and/or a semiconductor carrier. More specifically, the storage medium (212) may be a volatile memory or a non-volatile memory. For example, the volatile memory includes but not limited to a dynamic random access memory (DRAM) or a static random access memory (SRAM).

The communication module (31) is used for establishing a wireless communication channel between the physiological monitoring device (11) and the time calibration device (21). Preferably, the wireless communication channel may include but not limited to an infrared, Wi-Fi, Bluetooth, ANT, Zigbee, RFID, NFC, GSM (Global System for Mobile Communications), GPRS (General Packet Radio Service), UMTS (Universal Mobile Telecommunications System), LTE (Long Term Evolution), CDMA (Code Division Multiple Access) channel, or any wireless communication technology based on the optics, the magnetics, the electromagnetism or thereof. Or any other wireless communication technology that a person skilled in the art can understand.

Figure 2:
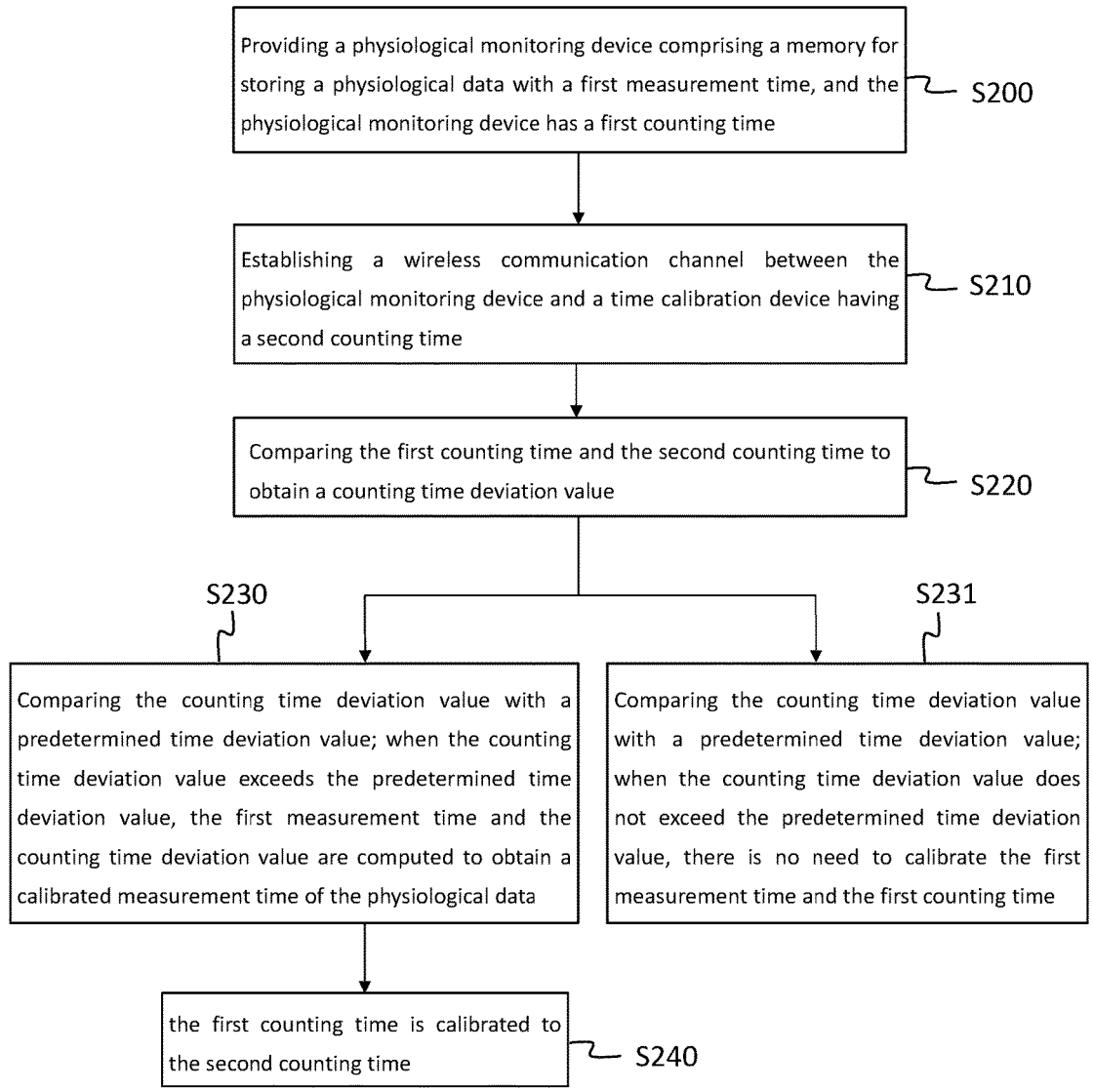
FIG. 2 is a flow chart of a preferred embodiment of a method for calibrating time of a physiological data according to the present invention.

FIG. 2 is a flow chart of a preferred embodiment of a method for calibrating time of a physiological data according to the present invention. Please refer to both FIG. 1 and FIG. 2, in the embodiment, first of all, physiological monitoring device (11) is provided in step (S200). The device comprises a memory (112) for storing a physiological data with a first measurement time, and the physiological monitoring device (11) has a first counting time. Preferably, the physiological monitoring device (11) is as described in above embodiments. More specifically, the physiological monitoring device (11) performs measurements and generates the physiological data. The data comprises a measured value and the first measurement time. The first measurement time is generated and recorded based on the first counting time when performing a measurement. Preferably, the first measurement time is the time point of measurement and/or duration of measurement. However, the invention is not limited thereto.

In step S210, a wireless communication channel is established between the physiological monitoring device (11) and a time calibration device (21). The time calibration device (21) has a second counting time. Preferably, the time calibration device (21) and the wireless communication channel are as described in above embodiments. The first counting time and the second counting time respectively indicate time of the physiological monitoring device (11) and time of the time calibration device (21). Units of the first counting time and the second counting time may include but not limited to year(s), month(s), day(s), hour(s), minute(s), second(s) or any combination thereof. A person skilled in the art can select an appropriate unit based on demand. More specifically, by establishing the wireless communication channel, the time calibration device (21) can access information in the physiological monitoring device (11). The information may include but not limited to the physiological data. In other words, the physiological data can be transmitted to the time calibration device (21) through the wireless communication channel.

In step S220, a counting time deviation value is obtained by comparing the first counting time and the second counting time. More specifically, since the physiological monitoring device (11) and the time calibration device (21) are independent devices, the first counting time and the second counting time may be different. For example, when the first counting time is 2015/07/31 09:30 and the second counting time is 2015/7/31 08:00, the counting time deviation value is 1 hr 30 mins. It's worth mentioning that if the physiological monitoring device (11) runs out of power or the power source is forcibly removed, the first counting time will stop counting. In other words, the first counting time of the physiological monitoring device (11) will be forced to stop temporarily, and when the power supply recovers, the first counting time can continue counting time from the time point at which the counting stops temporarily. Or, the physiological monitoring device may go back to default settings and restart its time counting function. Therefore, there may be an error or a delay in the first counting time, and may lead to an incorrect first measurement time in the physiological data.

In step S230, the counting time deviation value is compared with a predetermined time deviation value. When the counting time deviation value exceeds the predetermined time deviation value, the first measurement time and the counting time deviation value are computed to obtain a calibrated measurement time of the physiological data. Preferably, unit of the predetermined time deviation value may include but not limited to year(s), month(s), day(s), hour(s), minute(s), second(s) or any combination thereof. More specifically, the predetermined time deviation value may be a rule instruction stored in the storage medium (212). When the predetermined time deviation value is 1 hour and the counting time deviation value is 1 hr 30 mins, then the counting time deviation value exceeds the predetermined time deviation value. More specifically, when the counting time deviation value exceeds the predetermined time deviation value, the first measurement time of the physiological data is decided as an incorrect time, and time calibration is required.

As mentioned above, preferably, a calibrated measurement time obtained from computing the first measurement time and the counting time deviation value is obtained from addition or subtraction of the first measurement time and the counting time deviation value. For example, if the first measurement time is 2015/06/01 10:00, and the first counting time is later than the second counting time, then the calibrated measurement time value is obtained by deducting the counting time deviation value from the first measurement time value. That is, counting back 1 hr 30 mins from 2015/06/01 10:00, and the calibrated measurement time value is 2015/06/01 8:30.

For another example, when the first counting time is earlier than the second counting time, the calibrated measurement time value is equal to addition of the counting time deviation value to the first measurement time. That is, counting 1 hr 30 mins forward from 2015/06/01 10:00, and the calibrated measurement time value is 2015/06/01 11:30.

In step S240, the first counting time is calibrated to the second counting time. More specifically, when the counting time deviation value exceeds the predetermined time deviation value, the first counting time is decided as an incorrect time, and the first counting time is corrected to the time value of the second counting time and then the time counting continues. For example, if the first counting time is 2015/10/10 09:30 and the second counting time is 2015/10/10 09:00, the counting time deviation value is calculated as 30 mins and the predetermined time deviation value is 10 mins, then the first counting time is calibrated to 2015/10/10 09:00 and then the time counting continues.

In step S231, the counting time deviation value is compared with the predetermined time deviation value, and when the counting time deviation value does not exceed the predetermined time deviation value, there is no need to calibrate the first measurement time and the first counting time. More specifically, when the counting time deviation value does not exceeds the predetermined time deviation value, the first measurement time of the physiological data is determined as in a normal range of time and there is no need to perform time calibration. However, the invention is not limited thereto, and a person skilled in the art may change the rule for calibration based on demands. For example, calibration of the first counting time may not limited by comparison of the predetermined time deviation value and calibrating the first counting time to the second counting time. In other embodiments, when the wireless communication channel is established, the first counting time can be calibrated without comparison of a counting time deviation value or a predetermined time deviation value.

As mentioned above, in the rule for calibration the predetermined time deviation value for calibrating the first counting time and the predetermined time deviation value for calibrating the first measurement time may be different. More specifically, a second predetermined time deviation value is used for calibrating the first counting time. For example, the predetermined time deviation value for calibrating the first counting time may be 1 second, and the predetermined time deviation value for calibrating the first measurement time may be 1 hour. The counting time deviation value may be compared with different predetermined time deviation values and calibration of the first counting time and calibration of the first measurement time are performed separately.

Figure 3:
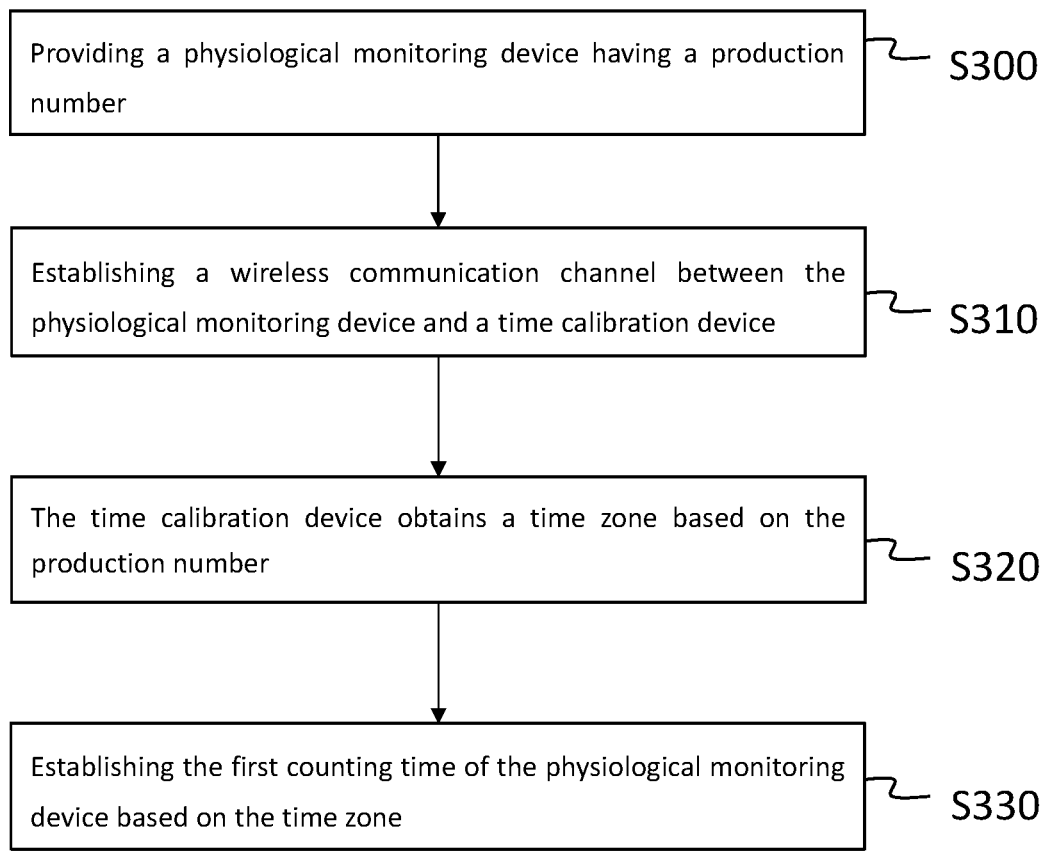
FIG. 3 is a flow chart of another preferred embodiment of a method for calibrating time of a physiological data according to the present invention.

FIG. 3 is a flow chart of another preferred embodiment of a method for calibrating time of a physiological data according to the present invention. Please refer to FIG. 1 to FIG. 3. In the embodiment, a physiological monitoring device (11) is provided first in step S300, and the physiological monitoring device (11) has a production number. Preferably, the physiological monitoring device (11) is as described in above embodiments. In addition, it should be noted that the production number may be used for identifying a production code of the physiological monitoring device (11). Preferably, coding of the production number may be based on date of manufacture, categories of manufacturer, place of manufacture, device, client, sales region or serial number, etc., but is not limited thereto.

In step S310, a wireless communication channel is established between the physiological monitoring device (11) and a time calibration device (21). Preferably, the time calibration device (21) may obtain information of the physiological monitoring device (11) (for example, the production number) through the wireless communication channel. In step S320, the time calibration device (21) obtains a time zone based on the production number. More specifically, the time calibration device (21) may obtain corresponding information based on the coding rule of the production number. For example, when the production number is TD201541C1, the coding rule of the character or number in the production number is as follows: "TD" represents for a code for manufacturer, "2015" indicates the year of manufacture, "41" indicates the category of device, and "C1" indicates the category of sales region. Preferably, category of sales region may correspond to one of the time zones, such that the time calibration device (21) may obtain a corresponding time zone.

In other embodiments, the time calibration device (21) may connect with a user profile through the production number for further obtaining the time zone. Preferably, the user profile is an internet account or an internet data. More preferably, the user profile has a password authentication protocol. For example, the user profile may include but not limited to name, gender, age, height, body weight, nation, the production number of the physiological monitoring device or time zone. The time zone may help to establish the initial setting of the user profile for a user, and it may be changed based on dynamic updates of the user profile. For example, the time zone in the user profile may be updated due to change in location of the user. More specifically, the time calibration device (21) further includes a positioning module (not shown) coupled to the microprocessor (211). The technology used in the positioning module may include but not limited to GPS (Global Positioning System) satellite positioning, bluetooth positioning, Wi-Fi positioning, BeiDou positioning, GPRS/CDMA (General Packet Radio Service/Code Division Multiple Access) mobile communication technology or any other positioning technology that a person skilled in the art can understand. The time zone of the user profile can be updated through the positioning result of the positioning module. However, the invention is not limited thereto.

In step S330, the first counting time of the physiological monitoring device (11) is established based on the time zone. More specifically, the time calibration device (21) can import standard time of the time zone to the physiological monitoring device (11) through the wireless communication channel, and set the standard time as the first counting time, such that the complex processes for entering time manually in initial settings for a user can be omitted, and possibilities of entering incorrect time can be eliminated.

In a preferred embodiment of the invention, a non-transitory computer-readable medium having an internally-stored program is provided, which performs a method for calibrating time of a physiological data when being executed in a microprocessor. The method comprises steps S210 to S240, and step S231. Preferably, the method may further comprise the step S320 and S330. However, the invention is not limited thereto.

In a preferred embodiment of the invention, a computer program product for calibrating time of a physiological data is provided, which completes methods mentioned above after being loaded and executed by a computer.

Although above embodiments have disclosed possible aspects of the method, system, non-transitory computer-readable medium and computer program product for calibrating time of a physiological data, a person skilled in the art should understand that designs of the method, system, non-transitory computer-readable medium and computer program product for calibrating time of a physiological data may be different among manufacturers. Therefore, the application of the present invention should not be limited to these possible configurations. In other words, as long as the following condition is fulfilled, it should be considered within the spirit of the present invention: a wireless communication channel is used for connecting different devices and counting time of different devices are compared to obtain a counting time deviation value, then the counting time deviation value is compared with a predetermined time to determine whether time calibration is necessary, such that the purpose of calibration the recorded time of a physiological data may be achieved. Several embodiments are further provided below for making a person skilled in the art further understands the spirit of the present invention and implements the invention.

In the embodiment of FIG. 1, the physiological monitoring device (10) is used for measuring at least one physiological parameter. However, it is only an alternative embodiment. In other embodiments, a person skilled in the art may choose an appropriated number and type of detection targets based on demands. Taking a drug test for example, the physiological detection device may detect a variety of targets, and the targets may be selected form a group consisting of cocaine (COC), tetrahydrocannabinol (THC), methamphetamine (MET), amphetamine (AMP), ecstasy (3,4-Methylenedioxymethamphetamine, MDMA), morphine (OPI), phencyclidine (PCP), benzodiazepines (BZO), barbiturates (BAR), methadone (MTD), tri-cyclic antidepressants (TCA), oxycodone (OXY) and any combination thereof. The above targets can be freely selected; however, detections of MET and AMP cannot be performed on a same test paper since they have similar structures and the detection results may be interfered.

As mentioned above, the memory (112) is used for storing the physiological data. More specifically, the memory (112) is used for storing the value of the physiological data and its corresponding measurement time, or duration of measurement. However, it is only an alternative embodiment. A person skilled in the art may change information items stored in the memory depending on demands. For example, the information items in the memory may include but not limited to corresponding parameters and related calibration parameters when the physiological monitoring device (11) performs measurements, and the expiration date, lot number, amount and expiration date after opening of the test strip used in the physiological monitoring device.

As mentioned above, the microprocessor (211) is disposed in the time calibration device (21) for comparing the first counting time and the second counting time to obtain a counting time deviation value, and for further comparing the counting time deviation value and a predetermined time deviation value, so as to determine whether to calibrate the time of the physiological data and/or the time of the physiological monitoring device (11). However, it is only an alternative embodiment. A person skilled in the art may change the disposed position of the microprocessor (211) depending on demands. For example, the microprocessor may be disposed in the physiological monitoring device (11).

As mentioned above, the physiological monitoring device (11) comprises a measurement module (111) and a first timer module (110), and the first timer module (110) has a first counting time. However, it is only an alternative embodiment. A person skilled in the art may change the type of the first timer module (for example, an independent module or an integrated module) depending on demands. For example, the first timer module may be an independent module which specifically performs time counting and does not have other functions. For another example, the first timer module may be integrated with a microprocessor, and time counting is one of the functions performed by the microprocessor, and the microprocessor may also give an instruction or performs other functions.

As mentioned above, the first counting time and the second counting time respectively indicate time of the physiological monitoring device (11) and time of the time calibration device (21). Units of the first counting time and the second counting time may include but not limited to year(s), month(s), day(s), hour(s), minute(s), second(s) or any combination thereof. In addition, unit of the predetermined time deviation value may include but not limited to year(s), month(s), day(s), hour(s), minute(s), second(s) or any combination thereof. However, it is only an alternative embodiment and a person skilled in the art may change the unit of time depending on demands. More specifically, the minimum unit of the predetermined time deviation value is not limited to 1 second. For example, unit of the predetermined time deviation value may be millisecond (ms), microsecond (μs), nanosecond (ns), picosecond (ps) or any time unit that the device can interpret.

As mentioned above, the physiological monitoring device (11), the time calibration device (21), and the communication module (31) are three independent devices, and the communication module (31) is used for establishing a wireless communication channel between the physiological monitoring device (11) and the time calibration device (21). However, it is only an alternative embodiment and a person skilled in the art may change the configuration of the communication module (31) depending on demands. For example, the communication module may comprise a sending end and a receiving end. The sending end may be disposed in the physiological monitoring device (11), and the receiving end may be disposed in the time calibration device (21).

In embodiments of FIG. 2, a wireless communication channel is established between the physiological monitoring device (11) and a time calibration device (21) in step S210. By establishing the wireless communication channel, the time calibration device (21) can access information in the physiological monitoring device (11). The information may include but not limited to the physiological data. In other words, the physiological data can be transmitted to the time calibration device (21) through the wireless communication channel. However, it is only an alternative embodiment and a person skilled in the art may change the contents of the accessing information as needed. For example, the accessing information can be the information stored in the memory (112), such as the physiological data, the messages of measuring procedure or operation error, the battery power of the physiological monitoring device, the date and time be set of the physiological monitoring device, or any information stored in the memory. Or the time calibration device (21) can transmit an instruction to the physiological monitoring device (11) by the wireless communication channel. The instructions may include but not limited to choose the test parameters, to update the test parameters, to calibrate the measuring time of the physiological data, to calibrate the setting time of the physiological monitoring device.

As mentioned above, preferably, the wireless communication channel is simplex communication, half-duplex communication or duplex communication. More specifically, the simplex communication is one-way transmission between the physiological monitoring device (11) and the time calibration device (21). The half-duplex communication is two-way transmission between the physiological monitoring device (11) and the time calibration device (21), but it only allows one direction transmission at the same time. In other words, if there are two directions signals need to transmit, it must be alternately. The duplex communication is two-way transmission between the physiological monitoring device (11) and the time calibration device (21) at all time, but the present invention shall not be limited for this.

As mentioned above, in order to avoid the time error possibility of the time calibration device (21), the method of the present invention further comprises calibrating the second counting time of the time calibration device to a standard time, and the standard time comes from a network server. In other words, the standard time of the network server can calibrate the second counting time of the time calibration device (21) to be a correct time. Preferably, the step described above can be performed repeatedly before or after the step S210 which is establishing a wireless communication channel between the physiological monitoring device and a time calibration device. A person skilled in the art may alter the step in the order of the method, the repeat number of the step, or the interval time between each repeat of the step as needed.

In embodiments of FIG. 1 and FIG. 2, after conducting a measurement by the physiological monitoring device (11), one or more physiological data record may be obtained. The physiological monitoring device (11) may comprise a memory (112) for storing the physiological data. However, it is only an alternative embodiment and a person skilled in the art may alter the source of the physiological data depending on demands. For example, the source of the physiological data is not limited to that measured by the physiological monitoring device, and the physiological data may be imported from other devices. Type of the imported physiological data may also be different from that measured by the physiological monitoring device.

In the embodiment of FIG. 3, a wireless communication channel is established between the physiological monitoring device (11) and a time calibration device (21) in step S310. Preferably, the time calibration device (21) may obtain the information of the physiological monitoring device (for example, a production number) through a wireless communication channel. However, it is only an alternative embodiment. More specifically, the time calibration device (21) may obtain the production number through automatic reading or manually entering by a user.

As mentioned above, the time calibration device (21) may connect with a user profile through the production number for further obtaining the time zone. The user profile may include but not limited to name, gender, age, height, body weight, nation, the production number of the physiological monitoring device or time zone. However, it is only an alternative embodiment, and a person skilled in the art may change the type and number of fields in the user profile depending on demands. For example, the number of fields of the production number of the physiological monitoring device may be three in total, and a user may separately enter three different production numbers of, for example, a blood glucose meter, a blood pressure meter, and an ear thermometer. Accordingly, the three different physiological monitoring devices can connect with the user profile through their respective production number, such that the time zone can be obtained and the first counting time of the blood glucose meter, the blood pressure meter, and the ear thermometer may be respectively obtained.

As mentioned above, the time calibration device (21) may obtain corresponding information based on the coding rule of the production number. For example, when the production number is TD201541C1, the coding rule of the character or number in the production number is as follows: "TD" represents for a code for manufacturer, "2015" indicates the year of manufacture, "41" indicates the category of device, and "C1" indicates the category of sales region. However, it is only an alternative embodiment, and a person skilled in the art may change the coding rule or add other different types of coding depending on demands.

In the embodiment of the FIG. 3, the time calibration device (21) may obtain information of the physiological monitoring device (11) (for example, the production number) through the wireless communication channel. The time calibration device (21) obtains a time zone based on the production number, and further establishes the first counting time of the physiological monitoring device (11) based on the time zone. However, it is only an alternative embodiment and the invention is not limited to obtaining the time zone through the production number. In other embodiments, a person skilled in the art may change the method for obtaining the time zone. For example, when a Subscriber Identity Module (or a SIM card for short) is inserted into the physiological monitoring device (11), the device can connect with the time calibration device (21), for example, a network server, through the internet so as to obtain the time zone where the network server is located. For another example, the microprocessor of the time calibration device may be configured to obtain the time zone for establishing the first counting time of the physiological monitoring device from the time zone of the network server or the present time zone of the physiological monitoring device. More specifically, when a user brings the physiological monitoring device to another different country and the network server is still located in the original country, after the physiological monitoring device is connected with the internet through a SIM card, the first counting time can be determined based on local time zone of the internet, or can be determined based on the time zone of the original network server. In other words, if the time calibration device is a network server, the physiological monitoring device and the time calibration device are located in different time zones, and the wireless communication channel is the internet, a person skilled in the art may set the microprocessor of the time calibration device as to use the time zone where the physiological monitoring device is located or to use the time zone where the time calibration device is located depending on demands.

In the embodiment of FIG. 3, the time calibration device (21) may further includes a positioning module coupled to the microprocessor (211), and the time zone of the user profile may be updated through the positioning result generated by the positioning module. However, it is only an alternative embodiment. A person skilled in the art may change the disposed position of the positioning module depending on demands. For example, the positioning module may be disposed in the physiological monitoring device, and the first counting time can be established based on the updated time zone according to the positioning result.

To sum up, the present disclosure relates to a method, a system, a non-transitory computer-readable medium and a computer program product for calibrating time of a physiological data, wherein a counting time deviation value may be obtained by comparison between different devices through a wireless communication, then the counting time deviation value is compared with a predetermined time deviation value to determine whether time calibration of the physiological data and/or the physiological monitoring device is necessary. Particularly, a production number of the physiological monitoring device may be further used for obtaining a counting time in initial settings. In addition, the preferred embodiments may have the following effects:

1. In the method for calibrating time of a physiological data provided in the present disclosure, a wireless communication channel is used as a route for comparing counting time of different devices and a predetermined time deviation value, such that steps for calibrating time manually and repeatedly by a button can be omitted, inconvenience and related costs derived from wired transmission can be eliminated, the portable range and the applicability of conducting other functions and the portable range of a physiological monitoring device when performing time calibration can be wider, problems generated from ignoring counting time errors of a physiological monitoring device by an user can be solved, convenience for a user is increased and a friendly user experience is created.

2. In the method for calibrating time of a physiological data provided in the present disclosure, the existing time record of the physiological data can be reviewed and corrected. In addition to calibrate the counting time of the physiological monitoring device itself to avoid generating physiological data with wrong time records in the future, possibilities of forgetting to calibrate errors in history time records can be further eliminated, and the correctness of time records of the physiological data at any time point can be ensured.

3. In the system for calibrating time of a physiological data provided in the present disclosure, the counting time of a time calibration device and a predetermined time deviation value are used as a basis for comparison for the counting time of a physiological monitoring device, such that risk of errors when entering calibrated time manually can be lowered, accuracy of time records of the physiological data can be elevated. A situation that may cause medication errors, such as a healthcare professional is unable to interpret a patient's condition because of the chaotic records of the measurement time of the physiological data and unable to timely modify the treatments based on the real condition of the patient that may cause medication errors, can be avoided.

4. In the non-transitory computer-readable medium having an internally-stored program and the computer program product provided in the present disclosure, a time zone can be obtained by a production number of a physiological monitoring device through a wireless communication channel, then is imported into the physiological monitoring device to establish the initial setting for counting time, such that steps such as setting year, month, day, hour and minute in first-time use of the physiological monitoring device can be simplified, time costs for a user to set the device can be shortened, and risk of errors in time setting can be reduced.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for calibrating time of a physiological data, which is adapted to a physiological monitoring device for measuring at least one physiological parameter, comprising:
    providing the physiological monitoring device comprising a memory for storing a physiological data with a first measurement time, and the physiological monitoring device having a first counting time;
    establishing a wireless communication channel between the physiological monitoring device and a time calibration device having a second counting time;
    comparing the first counting time and the second counting time to obtain a counting time deviation value;
    comparing the counting time deviation value with a predetermined time deviation value;
    calibrating the first measurement time of the physiological data, wherein when the counting time deviation value exceeds the predetermined time deviation value, the first measurement time and the counting time deviation value are computed to obtain a calibrated measurement time of the physiological data; and
    comparing the counting time deviation value and a second predetermined time deviation value, wherein the first counting time is calibrated to the second counting time when the counting time deviation value exceeds the second predetermined time deviation value.

2. The method according to claim 1, wherein calibrating the first measurement time of the physiological data further comprises:
    when the counting time deviation value does not exceed the predetermined time deviation value, there is no need to calibrate the first measurement time and the first counting time.

3. The method according to claim 1, wherein unit of the predetermined time deviation value is year(s), month(s), day(s), hour(s), minute(s), second(s), any combination thereof or any time unit which the time calibration device or the physiological monitoring device can recognize, and wherein the wireless communication channel is an infrared, Wi-Fi, Bluetooth, ANT, Zigbee, RFID, NFC, GSM, GPRS, UMTS, LTE, CDMA, any combination thereof or any wireless communication technology based on the optics, the magnetics or the electromagnetism and the wireless communication channel is simplex communication, half-duplex communication or duplex communication.

4. The method according to claim 1, wherein the calibrated measurement time obtained from computing the first measurement time and the counting time deviation value is obtained from addition or subtraction of the first measurement time and the counting time deviation value.

5. The method according to claim 1, wherein before or after the step of establishing the wireless communication channel between the physiological monitoring device and the time calibration device further comprises:
calibrating the second counting time of the time calibration device to a standard time, and the standard time comes from a network server.

6. The method according to claim 1, wherein after the step of establishing the wireless communication channel between the physiological monitoring device and the time calibration device further comprises:
transmitting the physiological data to the time calibration device.

7. The method according to claim 1, wherein the physiological parameter is obtained by performing a measurement directly on a living body or on an in vitro sample obtained from a living body and the physiological parameter is glucose, ketone, blood cell, blood pressure, haemoglobin, glycated haemoglobin (HbA1c), cholesterol, uric acid, urinary protein, lactate, temperature, body weight, blood oxygen level, hormone, electrocardiogram or any combination thereof.

8. The method according to claim 1, wherein when the counting time deviation value exceeds the predetermined time deviation value, the first counting time is calibrated to the second counting time.

9. The method according to claim 1, wherein the physiological monitoring device further comprises a production number, and after establishing the wireless communication channel,
a time zone is obtained by the time calibration device based on the production number; and
the first counting time of the physiological monitoring device is established based on the time zone.

10. A system for calibrating time of a physiological data, comprising:
a physiological monitoring device comprising:
a measurement module for measuring at least one physiological parameter;
a first timer module with a first counting time; and
a memory for storing a physiological data with a first measurement time;
a time calibration device comprising:
a second timer module with a second counting time; and
a microprocessor coupled to the second timer module; and
a communication module for establishing a wireless communication channel between the physiological monitoring device and the time calibration device; wherein when the wireless communication channel is established, the microprocessor is used for comparing the first counting time and the second counting time to obtain a counting time deviation value, and comparing the counting time deviation value with a predetermined time deviation value, and when the counting time deviation value exceeds the predetermined time deviation value, the first measurement time and the counting time deviation value are computed to obtain a calibrated measurement time of the physiological data; wherein the microprocessor is used for comparing the counting time deviation value and a second predetermined time deviation value, and the first counting time is calibrated to the second counting time when the counting time deviation value exceeds the second predetermined time deviation value.

11. The system according to claim 10, wherein unit of the predetermined time deviation value is year(s), month(s), day(s), hour(s), minute(s), second(s), any combination thereof or any time unit which the time calibration device or the physiological monitoring device can recognize, and wherein the wireless communication channel is an infrared, Wi-Fi, Bluetooth, ANT, Zigbee, RFID, NFC, GSM, GPRS, UMTS, LTE, CDMA, any combination thereof or any wireless communication technology based on the optics, the magnetics or the electromagnetism and the wireless communication channel is simplex communication, half-duplex communication or duplex communication, and wherein the physiological parameter is obtained by performing a measurement directly on a living body or on an in vitro sample obtained from a living body.

12. The system according to claim 10, wherein the calibrated measurement time obtained from computing the first measurement time and the counting time deviation value by the microprocessor is obtained from addition or subtraction of the first measurement time and the counting time deviation value.

13. The system according to claim 10, wherein the time calibration device is an electronic device which can obtain a standard time coming from a network server.

14. The system according to claim 10, wherein the wireless communication channel is used for transmitting the physiological data from the physiological monitoring device to the time calibration device.

15. The system according to claim 10, wherein the microprocessor compares the counting time deviation value with the predetermined time deviation value, and when the counting time deviation value does not exceed the predetermined time deviation value, the microprocessor determines not to calibrate the first measurement time and the first counting time.

16. The system according to claim 10, wherein the microprocessor compares the counting time deviation value and the predetermined time deviation value, and when the counting time deviation value exceeds the predetermined time deviation value, the microprocessor calibrates the first counting time to the second counting time.

17. The system according to claim 10, wherein the microprocessor further compares the counting time deviation value and a second predetermined time deviation value, and when the counting time deviation value exceeds the second predetermined time deviation value, the microprocessor calibrates the first counting time to the second counting time.

18. The system according to claim 10, wherein the physiological monitoring device has a production number, and the time calibration device is used for obtaining a time zone based on the production number, and the first timer module is used for establishing the first counting time based on the time zone.

19. A non-transitory computer-readable medium having an internally-stored program, which performs a method for calibrating time of a physiological data when being executed in a microprocessor, the method including:
    establishing a wireless communication channel between a physiological monitoring device and a time calibration device, wherein the physiological monitoring device has a first counting time, the time calibration device has a second counting time, and the physiological monitoring device is used for storing a physiological data with a first measurement time;
    comparing the first counting time and the second counting time to obtain a counting time deviation value;
    comparing the counting time deviation value with a predetermined time deviation value;
    calibrating the first measurement time of the physiological data, wherein when the counting time deviation value exceeds the predetermined time deviation value, the first measurement time and the counting time deviation value are computed to obtain a calibrated measurement time of the physiological data; and
    comparing the counting time deviation value and a second predetermined time deviation value, wherein the first counting time is calibrated to the second counting time when the counting time deviation value exceeds the second predetermined time deviation value.

20. The non-transitory computer-readable medium according to claim 19, wherein unit of the predetermined time deviation value is year(s), month(s), day(s), hour(s), minute(s), second(s), any combination thereof or any time unit which the time calibration device or the physiological monitoring device can recognize.

21. The non-transitory computer-readable medium according to claim 19, wherein the calibrated measurement time obtained from computing the first measurement time and the counting time deviation value is obtained from addition or subtraction of the first measurement time and the counting time deviation value.

22. The non-transitory computer-readable medium according to claim 19, wherein after comparing the counting time deviation value with the predetermined time deviation value,
    when the counting time deviation value does not exceed the predetermined time deviation value, there is no need to calibrate the first measurement time and the first counting time.

23. The non-transitory computer-readable medium according to claim 19, wherein when the counting time deviation value exceeds the predetermined time deviation value, the first counting time is calibrated to the second counting time.

24. The non-transitory computer-readable medium according to claim 19, wherein comparing the first counting time and the second counting time to obtain a counting time deviation value further comprises:
    comparing the counting time deviation value and a second predetermined time deviation value, and when the counting time deviation value exceeds the second predetermined time deviation value, the first counting time is calibrated to the second counting time.

25. The non-transitory computer-readable medium according to claim 19, wherein after establishing the wireless communication channel:
    a time zone is obtained based on a production number of the physiological monitoring device; and
    the first counting time of the physiological monitoring device is established based on the time zone.

26. A non-transitory computer readable medium including computer executable instructions, wherein the instructions, when executed by a processor, for calibrating time of a physiological data, which completes the method according to claims 19 after being loaded and executed by a computer.

* * * * *